United States Patent
Thompson et al.

(10) Patent No.: US 6,207,661 B1
(45) Date of Patent: Mar. 27, 2001

(54) PREMIXED FORMULATION OF PIPERACILLIN SODIUM AND TAZOBACTAM SODIUM INJECTION

(75) Inventors: Stacey S. Thompson, Wheeling; Rao Chilamkurti, Gurnee; Mary Samuel, Lindenhurst; Norma Stephens, Skokie, all of IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/255,513

(22) Filed: Feb. 22, 1999

(51) Int. Cl.[7] .................................................. A61K 31/43
(52) U.S. Cl. ............................................................ 514/192
(58) Field of Search ............................................. 514/192

(56) References Cited

U.S. PATENT DOCUMENTS

| | | | |
|---|---|---|---|
| 4,452,778 | 6/1984 | Brier | 424/114 |
| 4,477,452 | 10/1984 | Haeger | 424/250 |
| 4,534,977 | 8/1985 | Haeger | 514/196 |
| 4,535,078 | 8/1985 | Fox, Jr. et al. | 514/157 |
| 4,552,763 | 11/1985 | Brier | 424/114 |
| 4,562,073 | 12/1985 | Micetich et al. | 424/114 |
| 4,594,247 | 6/1986 | Brier | 424/114 |
| 4,837,317 | 6/1989 | Ratti | 540/316 |
| 5,650,421 | 7/1997 | Titus et al. | 514/370 |
| 5,763,603 | 6/1998 | Trickes | 540/310 |

FOREIGN PATENT DOCUMENTS

| | | |
|---|---|---|
| 0585987 | 3/1994 | (EP) . |
| 2179348 | 3/1987 | (FR) . |
| 2095551 | 10/1982 | (GB) . |

OTHER PUBLICATIONS

Mathew, M., et al., "Stability of Piperacillin Sodium in the Presence of Tazobactam Sodium in 5% Dextrose and Normal Saline Injections," *Journal of Clinical Pharmacy and Therapeutics,* vol. 19, 1994, pp. 397–399, XP00900664.

Bird, A., et al., "N–Formylpnicillamine and Penicillamine as Degradation Products of Penicillins in Solution," *Journal of Pharm. Pharmacol.*, vol. 38, No.12, 1986, pp. 913–916, XP000900666.

Yamana, T., et al., "Stability Kinetics of Piperacillin in Aqueous Solutions," *International Journal of Pharmaceutics,* 11 (1982) pp. 71–80.

Primary Examiner—Kevin E. Weddington
(74) Attorney, Agent, or Firm—Mark J. Buonaiuto; Joseph A. Fuchs

(57) ABSTRACT

The present invention provides a premixed form of a buffered piperacillin product having a near neutral pH and capable of a shelf life of at least nine months, with freezer storage (−20° C. or lower), or a refrigerated shelf life of up to 14 days at about 5° C. The piperacillin may additionally contain a tazobactam component to inactivate beta-lactamases that commonly cause resistance to penicillins, allowing the piperacillin component to destroy susceptible bacteria. With the addition of dextrose, the premixed composition is physiologically isosmotic.

42 Claims, No Drawings

PREMIXED FORMULATION OF PIPERACILLIN SODIUM AND TAZOBACTAM SODIUM INJECTION

TECHNICAL FIELD

This invention relates to pharmaceutical compositions, and more specifically to a liquid premix formulation of piperacillin sodium and tazobactarn sodium. The liquid premix formulation is suitable for intravenous administration and has a viable shelf-life.

BACKGROUND ART

Polymicrobial infections often include pathogens that produce beta-lactamase enzymes. These enzymes commonly cause resistance to penicillins and cephalosporins. Without treatment these enzymes would multiply and thrive unimpeded, with serious or critical consequences to the patient.

To treat such infections, a product consisting of piperacillin sodium and tazobactam sodium in an 8 to 1 ratio (as free acids), is currently marketed under the tradename Zosyn®. This product is disclosed in U.S. Pat. No. 4,562,073 to Micetich et al. However, because piperacillin is inherently unstable in solution at room temperature, like most penicillin compounds, Wyeth-Ayerst Research developed Zosyn® as a lyophilized vial product where the piperacillin is stored in the solid state.

In use, the piperacillin component offers the safety and efficacy of a broad-spectrum beta-lactam antibiotic. U.S. Pat. Nos. 4,477,452 and 4,534,977, both to Haeger, disclose a lyophilized form of piperacillin. Tazobactam reduces the vulnerability of the piperacillin to the bacteria that produce beta-lactamase enzymes. Basically, the tazobactam permanently inactivates beta-lactamases, allowing the piperacillin component to destroy susceptible bacteria. However, Zosyn® is supplied in a lyophilized form and therefore must be reconstituted prior to intravenous administration.

Zosyn® is a relatively potent antibiotic. It is used for the treatment of moderate to severe infections caused by piperacillin-resistant, piperacillin/tazobactam-susceptible beta-lactamase-producing strains of microorganisms in conditions such as nosocomial pneumonia due to *Staphylococcus aureits*; intra-abdominal infections, specifically appendicitis (complicated by rupture or abscess) and peritonitis due to *Escherichia coli*, skin and skin structure infections, including cellulitits, cutaneous abscesses and ischemic/diabetic foot infections due to *Staphylococcus acreus*; and gynecologic infections, specifically postpartum endometritis or pelvic inflammatory disease due to *Escherichia coli*. The seriousness of these infections highlights the need for a readily available and dependable treatment.

The admixing required by the lyophilized vial product is a skilled pharmaceutical procedure that must be performed using aseptic techniques to ensure product quality. This step creates the possibility of contamination and dosage miscalculation. It also adds to the cost of preparing the Zosyn® for administration. The laborious and difficult technique of lyophilizing and reconstituting the drug is addressed in U.S. Pat. No. 5,763,603 to Trickes. While the Trickes reference does teach a process of increasing the stability of tazobactam, such is accomplished by crystallization rather than in a buffered pH solution.

Another drawback of the reconstituted product is reflected in its short refrigerated shelf life. The reconstituted product remains stable and commercially viable for only seven days while refrigerated according to the manufacturer's product labeling (See also *Physicians' Desk Reference*, Medical Economics Company, Inc., pp. 1434–37 (52 ed., 1998)). The short shelf life and the reconstitution step may also lead to increased waste disposal as the components required to prepare the reconstituted solution, such as vials, needles and bags, as well as unused portions of the product, must be properly discarded.

Finally, another concern with the lyophilized powder vial product is that after reconstitution it has a pH more acidic than 6.5. This acidic condition increases the potential for hemolysis and pain to the patient during infusion.

The formulations of the present invention overcome the disadvantages of the reconstituted product as they are premixed and stable for longer periods at refrigerated temperature. Additionally, any potential for problems of contamination, needle sticks, increased waste, and dosage calculation errors are avoided, as medical personnel can simply use a prepared bag of the present formulations.

SUMMARY OF THE INVENTION

A new liquid form of premixed piperacillin for use in parenteral administration to fight polymicrobial infection in patients is disclosed. In providing the present premix many disadvantages of the prior art can be avoided. Such disadvantages include possible contamination, increased waste disposal, dosage calculation errors, and drug instability to name a few.

In one embodiment of the present invention the piperacillin, as piperacillin sodium, in a solution of suitable liquid, is brought within a suitable pH range. The pH, and therefore the stability of the solution, can be maintained by buffering the formulation with a suitable quantity of a citrate.

In another embodiment of the present invention, an effective amount of tazobactam, as tazobactam sodium, is included with the buffered piperacillin solution. The pH of this embodiment is also maintained within a particular range.

In still another embodiment, any of the previous embodiments may be made physiologically iso-osmotic (a.k.a., isosmotic) with the addition of dextrose hydrous or dextrose anhydrous.

The stability of the formulations allows the present invention to be stored for at least nine months at −20° C. or below. Before use the frozen formulation is thawed and remains viable for one day at room temperature. Alternatively, the formulations may be stored at a refrigerated temperature (5° C.±3° C.) for as long as 14 days and remain viable according to the premix product labeling. This is enhanced stability compared to the reconstituted vial product, which is only viable for seven (7) days while refrigerated according to the manufacturer's product labeling.

Other advantages and aspects of the present invention will become apparent upon reading the following detailed description of the invention.

Detailed Disclosure

While the invention is susceptible of embodiment in many different forms, this disclosure will described in detail preferred embodiments of the invention with the understanding that the present disclosure is to be considered as an exemplification of the principles of the invention and is not intended to limit the broad aspect of the invention to the embodiments illustrated.

The present inventive formulations offer a number of advantages over other forms of piperacillin and piperacillin/tazobactam administration. For example, the premixed solution demonstrates long-term stability and enhanced shelf life when prepared at a physiologically suitable pH range. The long-term stability of piperacillin in solution was not known before the present invention. The stability of the formulation is achieved by buffering the solution with citrate to maintain the pH range.

Another example is that the formulations of the present invention are premixed so that they are ready for immediate use upon thawing. This eliminates the requirement to perform an admixture, along with the problems inherent to such a process.

Piperacillin free acid is the preferred source of piperacillin for use in the present invention. The free acid is converted to the sodium salt during the formulation process. Piperacillin sodium is derived from D(−)-α-aminobenzylpenicillin. The chemical name of piperacillin sodium is sodium (2S, 5R, 6R)-6-[(R)-2-(4-ethyl-2,3-dioxo-1-piperazinecarboxamido)-2-phenylacetamido]-5 3,3-dimethyl-7-oxo-4-thia-1-azabicyclo (3.2.0) heptane-2-carboxylate, with a chemical formula of $C_{23}H_{26}N_5NaO_7S$ and a molecular weight of 539.6. Piperacillin free acid was obtained in powder form from Wyeth-Ayerst. The piperacillin free acid is preferably mixed with a quantity of deionized water, and neutralized with sodium bicarbonate or other suitable agents, to bring the concentration of the solution within the preferred range of 20 to 80 mg/ml, more preferably within the range of 30 to 70 mg/ml, and most preferably within the range of 38 to 62 mg/ml or any combination or subcombination of ranges therein.

Tazobactam free acid is the preferred source of tazobactam for use in the present invention. The free acid is converted to the sodium salt during the formulation process. Tazobactam sodium, a derivative of the penicillin nucleus, is a penicillanic acid sulfone. Its chemical name is sodium (2S, 3S, 5R)-3-methyl-7-oxo-3-(1H- 1, 2, 3 -triazol-1-ylmethyl)-4-thia-1-azabicyclo-(3,2,0)heptane-2-carboxylate-4,4-dioxide. The chemical formula for tazobactam sodium is $C_{10}H_{11}N_4NaO_5S$ and the molecular weight is 322.3. The tazobactam free acid was supplied in powdered form through Wyeth-Ayerst. Tazobactam free acid is to be added to the piperacillin solution to create a concentration of tazobactam sodium to within a preferable range of 0.0 to 9.0 mg/ml, more preferably within the range of 4.0 to 8.0 mg/ml, and most preferably within the range of 4.8 to 7.8 mg/ml, or any range or subcombination of ranges therein.

The total concentration of piperacillin sodium and tazobactam sodium in solution is preferably within the range of 20 to 89 mg/ml. More preferably the total concentration is within the range of 34 to 78 mg/ml, and most preferably within the range of 42.8 to 69.8 mg/ml, or any range or subcombination of ranges therein. These quantities allow for an effective amount of piperacillin or piperacillin/tazobactam to be delivered in common dosage amounts of 50 to 250 ml.

The resulting piperacillin or piperacillin/tazobactam solution is then brought to within a preferred pH range of 6.1 to 6.9, and more preferably within the range of 6.3 to 6.7. In a preferred form of the invention the pH of the solution is about 6.5. Hydrochloric acid or other suitable acid can be used to adjust the pH downward, and sodium bicarbonate, or other suitable base, can be used to adjust the pH upward.

To maintain the pH within the preferred range, the solution is buffered with citrate or other suitable buffers. Citrate is the preferred buffer because it can maintain the pH of the solution without significant drug degradation. When using such buffers as phosphate, the pH cannot be maintained in the frozen state (See "Effect Of Freezing On The pH And Composition Of Sodium And Potassium Phosphate Solutions: The reciprocal system $KH_2PO_4$—$Na_2HPO_4$—$H_2O$," L. Van den Berg and D. Rose, Arch. Biochem. Biophys., 81, p. 319 (1959)). The addition of a buffer is desired for controlling the pH to enhance stability. A suitable amount of sodium citrate used to buffer the formulation controls the pH for maximum stability without significantly catalyzing or degrading the drug, or causing pain to the patient upon infusion. [A clinical study was performed to confirm the absence of patient pain upon infusion.]

Sodium citrate dihydrate is the preferred form for the buffer used in the present invention. The amount of sodium citrate dihydrate is preferably within the range of 1 to 4 mg/ml, more preferably within the range of 1.5 to 3.5 mg/ml, and most preferably within the range of 1.8 to 3.2 mg/ml or any range or subcombination of ranges therein.

It may also be desirable to add dextrose to the solution to render the solution physiologically isosmotic (approximately 300 mOsmol/kg). Dextrose hydrous or anhydrous can be used in the present invention. The concentration of the dextrose hydrous is within the preferred range of 5 to 30 mg/ml, and more preferably within the range of 6 to 22 mg/ml or any combination or subcombination or ranges therein.

After complete formulation and mixing, the premixed piperacillin or piperacillin/tazobactam solution is placed into suitable dosage containers. Suitable containers include those sold by Baxter under the tradename GALAXY®. The containers are then stored in a freezer at −20° C. or lower. Studies have shown that the formulations of the present invention remain viable for at least nine months while frozen.

Before use the frozen containers should be thawed in a conventional manner. The formulations will remain viable at room temperature for one day after removal from the freezer. Alternatively, the containers may be refrigerated at about 5° (±3° C.) for as much as 14 days.

Under careful study, the stability of different formulations during long-term frozen and short-term thawed storage was assessed. Various formulations were evaluated to ascertain which combinations of components had long-term stability. Parameters assessed included drug concentration, impurities, solution pH, solution color, visual appearance, osmolality, citrate concentration, and particulate matter. Formulations were either unbuffered or buffered with sodium citrate dihydrate. Various solution pHs were evaluated as well. Preferred formulations were stored for up to nine months frozen.

Illustrative, non-limiting examples of the present formulations are set out in TABLE 1 below. Numerous other examples can readily be envisioned in light of the guiding principles and teachings contained herein. For example, the solution pH could be varied, but remain in the zone of the desired long-term drug stability period; the dextrose concentration can be varied slightly and still allow the formulation to be isosmotic; and the citrate buffer concentration can be varied, but retain sufficient buffer capacity without causing pain on infusion. The examples given herein are intended to illustrate the invention and not in any sense to limit the manner in which the invention can be practiced.

TABLE 1

| Component | Dosage→ 2.25 g/50 mL Contents per 50 mL | 4.5 g/100 mL Contents per 100 mL | 3.375 g/50 mL Contents per 50 mL |
| --- | --- | --- | --- |
| Piperacillin (as piperacillin sodium) | 2 g | 4 g | 3 g |
| Tazobactam (as tazobactam sodium) | 0.25 g | 0.5 g | 0.375 g |
| Dextrose Hydrous, USP | 1 g | 2 g | 350 mg |
| Sodium Citrate Dihydrate, USP | 100 mg | 200 mg | 150 mg |
| Sodium Bicarbonate, USP | | for pH adjustment | |
| Hydrochloric Acid, NF | | for pH adjustment | |
| Water for Injection, USP | Q.S. | Q.S. | Q.S. |

While specific embodiments have been illustrated and described, numerous modifications are possible without departing from the spirit of the invention, and the scope of protection is only limited by the scope of the accompanying claims.

We claim:

1. A pharmaceutical composition suitable for administration parenterally, comprising a buffered solution having an effective amount of piperacillin and a pH adjusted to be in the range of from about 6.1 to about 6.9.

2. The pharmaceutical composition of claim 1 wherein the effective amount of piperacillin is provided in the form of piperacillin sodium, and wherein the concentration of piperacillin is within the range of from about 20 to about 80 mg/ml of solution.

3. The pharmaceutical composition of claim 2 wherein the concentration of piperacillin within the range of about 30 to about 70 mg/ml of solution.

4. The pharmaceutical composition of claim 2 wherein the concentration of piperacillin is within the range of about 38 to about 62 mg/ml of solution.

5. The pharmaceutical composition of claim 1 wherein the pH is adjusted to about 6.5.

6. The pharmaceutical composition of claim 1 further comprising a buffer.

7. The pharmaceutical composition of claim 6 wherein the buffer is a citrate.

8. The pharmaceutical composition of claim 7 wherein the buffer is sodium citrate.

9. The pharmaceutical composition of claim 8 wherein the concentration of the sodium citrate buffer is within the range of from about 1 to about 4 mg/ml of solution.

10. The pharmaceutical composition of claim 9 wherein the concentration of the sodium citrate buffer is within the range of from about 1.5 to about 3.5 mg/ml of solution.

11. The pharmaceutical composition of claim 9 wherein the concentration of the sodium citrate buffer is within the range of from about 1.8 to about 3.2 mg/ml of solution.

12. The pharmaceutical composition of claim 1 further comprising an effective amount of tazobactam.

13. The pharmaceutical composition of claim 12 wherein the effective amount of tazobactam is provided in the form of tazobactam sodium, and wherein the concentration of tazobactam is within the range of from about 0.0 to about 9.0 mg/ml of solution.

14. The pharmaceutical composition of claim 13 wherein the concentration of tazobactam is within the range of from about 4 to about 8 mg/ml of solution.

15. The pharmaceutical composition of claim 13 wherein the concentration of tazobactam is within the range of from about 4.8 to about 7.8 mg/ml of solution.

16. The pharmaceutical composition of claim 12 wherein the pH is adjusted to about 6.5.

17. The pharmaceutical composition of claim 16 further comprising a buffer.

18. The pharmaceutical composition of claim 17 wherein the buffer is a citrate.

19. The pharmaceutical composition of claim 18 wherein the buffer is sodium citrate.

20. The pharmaceutical composition of claim 19 wherein the concentration of the sodium citrate buffer is within the range of from about 1 to about 4 mg/ml of solution.

21. The pharmaceutical composition of claim 20 wherein the concentration of the sodium citrate buffer is within the range of from about 1.5 to about 3.5 mg/ml of solution.

22. The pharmaceutical composition of claim 20 wherein the concentration of the sodium citrate buffer is within the range of from about 1.8 to about 3.2 mg/ml of solution.

23. The pharmaceutical composition of claim 1 further comprising an effective amount of dextrose to render the composition physiologically isosmotic.

24. The pharmaceutical composition of claim 23 wherein the concentration of dextrose is within the range of from about 5 to about 30 mg/ml of solution.

25. The pharmaceutical composition of claim 24 wherein the concentration of dextrose is preferably within the range of from about 6 to about 22 mg/ml of solution.

26. A process of making a pharmaceutical piperacillin composition having a refrigerated shelf life in excess of 7 days, comprising the steps of:
   a. dissolving an effective amount of piperacillin into a suitable liquid forming a premixed solution;
   b. adjusting the pH of the premixed solution to a range of from about 6.1 to about 6.9;
   c. filling suitable containers with the premixed solution; and
   d. storing the containers of premixed solution in a suitable atmosphere at about 5° C. ±3° C.

27. The process of claim 26 further comprising the step of dissolving an effective amount of tazobactam into the premixed solution.

28. The process of claim 26 further comprising the step of buffering the solution.

29. The process of claim 26 wherein the suitable atmosphere is −20° C. or lower.

30. The process of claim 26 further comprising the step of adding an amount of dextrose to the premixed solution to make the composition physiologically isosmotic.

31. The process of claim 26 wherein the effective amount of piperacillin is provided by piperacillin sodium at a concentration within the range of from about 20 to about 80 mg/ml of suitable liquid.

32. The process of claim 31 wherein the concentration of the piperacillin is within the range of from about 30 to about 70 mg/ml of suitable liquid.

33. The process of claim 31 wherein the concentration of the piperacillin is within the range of from about 38 to about 62 mg/ml of suitable liquid.

34. The process of claim 27 wherein the effective amount of tazobactam is provided by tazobactam sodium at a concentration within the range of from about 0.0 to about 9.0 mg/ml of suitable liquid.

35. The process of claim 34 wherein the concentration of the tazobactam is within the range of from about 4 to about 8 mg/ml of suitable liquid.

36. The process of claim 34 wherein the concentration of the tazobactam is within the range of from about 4.8 to about 7.8 mg/ml of suitable liquid.

37. The process of claim 27 further comprising the step of buffering the solution.

38. The process of claim 37 wherein the step of buffering the premixed solution includes the step of adding an effective amount of a citrate to the premixed solution.

39. The process of claim 38 where the citrate includes sodium citrate and is within the range of from about 1 to about 4 mg/ml of suitable liquid.

40. The process of claim 38 where the citrate includes sodium citrate and is within the range of from about 1.5 to about 3.5 mg/ml of suitable liquid.

41. The process of claim 38 where the citrate includes sodium citrate and is within the range of from about 1.8 to about 3.2 mg/ml of suitable liquid.

42. The process of claim 26 wherein the pH of the premixed solution is about 6.5.

\* \* \* \* \*